(12) United States Patent
Veyland et al.

(10) Patent No.: US 9,550,891 B2
(45) Date of Patent: Jan. 24, 2017

(54) RUBBER COMPOSITION COMPRISING A THIAZOLINE DERIVATIVE

(75) Inventors: Anne Veyland, Clermont-Ferrand (FR); Nicolas Seeboth, Clermont-Ferrand (FR)

(73) Assignees: Compagnie Generale Des Etablissements Michelin, Clermont-Ferrand (FR); Michelin Recherche Et Technique S.A., Granges-Paccot (CH)

( * ) Notice: Subject to any disclaimer, the term of this patent is extended or adjusted under 35 U.S.C. 154(b) by 344 days.

(21) Appl. No.: 14/111,606

(22) PCT Filed: Apr. 16, 2012

(86) PCT No.: PCT/EP2012/056905
§ 371 (c)(1),
(2), (4) Date: Dec. 20, 2013

(87) PCT Pub. No.: WO2012/140254
PCT Pub. Date: Oct. 18, 2012

(65) Prior Publication Data
US 2014/0107268 A1    Apr. 17, 2014

(30) Foreign Application Priority Data
Apr. 14, 2011  (FR) ..................... 11 01171

(51) Int. Cl.
| | | |
|---|---|---|
| C08L 9/06 | (2006.01) | |
| C08K 13/02 | (2006.01) | |
| B60C 1/00 | (2006.01) | |
| C07D 277/16 | (2006.01) | |
| C08K 5/00 | (2006.01) | |
| C08K 5/46 | (2006.01) | |
| C08K 5/47 | (2006.01) | |

(52) U.S. Cl.
CPC ............... *C08L 9/06* (2013.01); *B60C 1/0016* (2013.04); *C07D 277/16* (2013.01); *C08K 5/0025* (2013.01); *C08K 5/46* (2013.01); *C08K 5/47* (2013.01); *C08K 13/02* (2013.01)

(58) Field of Classification Search
CPC .................... C08K 13/02; C08L 9/06
USPC .................... 524/186, 322; 548/186
See application file for complete search history.

(56) References Cited

U.S. PATENT DOCUMENTS

| | | | | |
|---|---|---|---|---|
| 2,196,607 | A |   | 4/1940 | Mathes ............ 260/302 |
| 2,782,139 | A | * | 2/1957 | Hill ............ C08J 5/06 |
| | | | | 156/910 |
| 2,866,778 | A | * | 12/1958 | Leshin ............ C08K 5/0025 |
| | | | | 525/332.7 |
| 3,040,053 | A | * | 6/1962 | D Amico ............ C07D 277/74 |
| | | | | 525/349 |
| 3,379,678 | A |   | 4/1968 | Greco et al. ............ 260/45.8 |
| 3,938,574 | A |   | 2/1976 | Burmester et al. ....... 152/330 R |
| 5,977,238 | A |   | 11/1999 | Labauze ............ 524/492 |
| 6,013,718 | A |   | 1/2000 | Cabioch et al. ............ 524/506 |
| 6,503,973 | B2 |  | 1/2003 | Robert et al. ............ 524/492 |
| 6,774,255 | B1 |  | 8/2004 | Tardivat et al. ............ 556/427 |
| 6,815,473 | B2 |  | 11/2004 | Robert et al. ............ 523/215 |
| 7,217,751 | B2 |  | 5/2007 | Durel et al. ............ 524/262 |
| 7,300,970 | B2 |  | 11/2007 | Durel et al. ............ 524/493 |
| 7,312,264 | B2 |  | 12/2007 | Gandon-Pain ............ 524/236 |
| 7,488,768 | B2 |  | 2/2009 | Tardivat et al. ............ 524/262 |
| 7,491,767 | B2 |  | 2/2009 | Durel et al. ............ 524/493 |
| 7,820,771 | B2 |  | 10/2010 | Lapra et al. ............ 525/479 |
| 7,900,667 | B2 |  | 3/2011 | Vasseur ............ 152/209.1 |
| 8,344,063 | B2 |  | 1/2013 | Marechal et al. ............ 524/571 |

(Continued)

FOREIGN PATENT DOCUMENTS

BE   503980 A   6/1951
BE   503980 A   10/1952

(Continued)

OTHER PUBLICATIONS

F. D. Stewart, et al., "Synthesis of Derivatives of 4,5-Dimethyl-2-Mercaptothiazole", J. Org. Chem., vol. 14, pp. 1111-1117 (1949).

(Continued)

*Primary Examiner* — Ling Choi
*Assistant Examiner* — Ronald Grinsted
(74) *Attorney, Agent, or Firm* — Fitzpatrick, Cella, Harper & Scinto

(57) ABSTRACT

A rubber composition for manufacturing tyres includes one or more diene elastomers, one or more reinforcing fillers, and a vulcanization system. The vulcanization system includes one or more thiazoline compounds chosen from compounds of formula I and compounds of formula II:

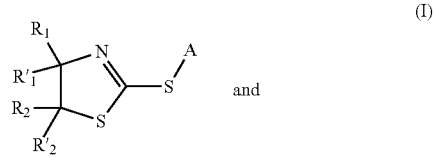

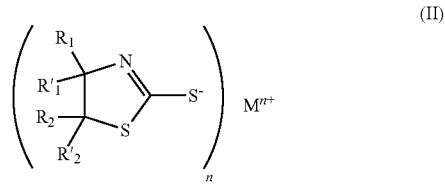

Certain specific thiazoline derivatives are described.

27 Claims, No Drawings

(56) References Cited

U.S. PATENT DOCUMENTS

| | | |
|---|---|---|
| 8,455,584 B2 | 6/2013 | Robert et al. ............. 524/505 |
| 2001/0036991 A1 | 11/2001 | Robert et al. ............. 524/492 |
| 2002/0183436 A1 | 12/2002 | Robert et al. ............. 524/592 |
| 2004/0051210 A1 | 3/2004 | Tardivat et al. ........... 264/349 |
| 2004/0132880 A1 | 7/2004 | Durel et al. .............. 524/262 |
| 2005/0016650 A1 | 1/2005 | Durel et al. ............ 152/209.1 |
| 2005/0016651 A1 | 1/2005 | Durel et al. ............ 152/209.1 |
| 2005/0267247 A1* | 12/2005 | Steger .............. C08K 5/0025 524/492 |
| 2006/0089445 A1 | 4/2006 | Gandon-Pain ............. 524/492 |
| 2007/0112120 A1 | 5/2007 | Vasseur ................... 524/492 |
| 2008/0132644 A1 | 6/2008 | Lapra et al. .............. 525/105 |
| 2009/0186961 A1 | 7/2009 | Araujo Da Silva et al. . 523/150 |
| 2009/0209709 A1 | 8/2009 | Araujo Da Silva et al. ........... 525/333.1 |
| 2009/0234066 A1 | 9/2009 | Araujo Da Silva et al. . 524/571 |
| 2009/0270558 A1 | 10/2009 | Gandon-pain et al. ....... 525/190 |
| 2010/0184912 A1 | 7/2010 | Marechal et al. ........... 524/571 |
| 2010/0249270 A1 | 9/2010 | Robert et al. .............. 523/150 |
| 2010/0252156 A1 | 10/2010 | Robert et al. ............ 152/209.1 |
| 2011/0152458 A1 | 6/2011 | Araujo Da Silva et al. . 525/102 |

FOREIGN PATENT DOCUMENTS

| | | |
|---|---|---|
| EP | 1 127 909 A1 | 8/2001 |
| FR | 2 740 778 A1 | 5/1997 |
| FR | 2 765 882 A1 | 1/1999 |
| WO | 97/36724 | 10/1997 |
| WO | 99/16600 | 4/1999 |
| WO | 01/92402 A1 | 12/2001 |
| WO | 02/10269 A2 | 2/2002 |
| WO | 02/30939 A1 | 4/2002 |
| WO | 02/31041 A1 | 4/2002 |
| WO | 02/083782 A1 | 10/2002 |
| WO | 03/002648 A1 | 1/2003 |
| WO | 03/002649 A1 | 1/2003 |
| WO | 03/16837 A1 | 2/2003 |
| WO | 2004/096865 A2 | 11/2004 |
| WO | 2006/069792 A1 | 7/2006 |
| WO | 2006/069793 A1 | 7/2006 |
| WO | 2006/125532 A1 | 11/2006 |
| WO | 2006/125533 A1 | 11/2006 |
| WO | 2006/125534 A1 | 11/2006 |
| WO | 2008/038175 A2 | 4/2008 |
| WO | 2008/141702 A1 | 11/2008 |
| WO | 2009/000750 A1 | 12/2008 |
| WO | 2009/000752 A1 | 12/2008 |

OTHER PUBLICATIONS

A. Z. Rys, et al., "Insertion of a Two Sulfur Unit Into the S-S Bond-Tailor-Made Polysulfides", Tetrahedron Letters, vol. 41, pp. 7169-7172 (2000).
S. F. Birch, et al., "The Preparation and Properties of Di-Alkyl Di- and Poly-Sulphides. Some Disproportionation Reactions", Journal of the Institute of Petroleum, vol. 39, pp. 206-210 (1953).
E. Brzezinska, et al., "Disulfides. 1. Syntheses Using 2,2'-Dithiobis(benzothiazole)", J. Org. Chem., vol. 59, pp. 8239-8244 (1994).
R. Taylor, "The Mechanism of Thermal Eliminations. Part 15. Abnormal Rate Spread in Pyrolysis of Alkyl Methyl Carbonates and S-Alkyl O-Methyl Carbonates due to Enhanced Nucleophilicity of the Carbonyl Group", J. Chem. Soc. Perkin Trans. II, pp. 291-296 (1983).
S. Suzuki, et al., "NMR Studies and Structural Assignment of Paederoside", Heterocycles, vol. 35, No. 2, pp. 895-900 (1993).
H. W. Chen, et al., "Sulfur Chelates. 31. Synthesis and Characterization of Aryl Xanthogens, Xanthate Esters, and Esters of O-Aryl S-Alkyl Thiocarbonates. Synthesis and Single-Crystal X-Ray Structure of a Polymeric Xanthogen Complex of Copper (I), [CuCl(S2COC6H4-4-CH3)2]n", J. Amer. Chem. Soc., vol. 100, pp. 2370-2375 (1978).
M. Bhalla, et al., "Synthesis and Pharmacological Evaluation of 1,2,4-triazine and its Congeners", Bollettino Chimico Farmaceutico, vol. 134, No. 1, pp. 9-15 (1995).
M. Mikolajczyk, et al., "Synthesis and Pummerer Rearrangement of B-Phosphoryl Sulphoxides", Tetrahedron, vol. 39, No. 7, pp. 1189-1193 (1983).
W. F. Hart, et al., "Thiazolinephenols. 5-Methyl- and 5,5-Dimethylthiazolinephenols, By-products and Derivatives", J. Amer. Chem. Soc. vol. 61, pp. 1145-1148 (1939).
M. Gianturco, et al., "Some Mercaptotriazines", Gazzetta Chimica Italiana, vol. 82, pp. 429-434 (1953).
M. Tisler, "Syntheses and Structure of Some 5-Substituted 2,3-Dihydro-1,2,4-triazine-3-thiones", Croatica Chemica Acta, vol. 32, pp. 123-132 (1960).
L.M. Mironovich, et al., "Oxidation of Substituted 2H,4H-1,2,4-Triazine-3-Thion-5-Ones", Ukrainian Chem. J., vol. 62, pp. 58-59 (1996).
J. Wieczorek, et al., "Antifungal Properties of a Novel 1,2,4-Triazine Derivative I 319", Archivum Immunologiae et Therapiae Experimentalis, vol. 28, pp. 727-733 (1980).
Translation of S.S. Smagin, et al., "Synthesis and Neuropharmarcological Activity of 1,2,4-Triazine-3-Thione Derivatives", Khimiko-Farmatsevticheskii Zhurnal, vol. 9, No. 4, pp. 11-15 (1975).
J. Kralovsky, et al., "Use of Asymmetric Triazines in Analytical Chemistry. III. Constitution of Asymmetric Monoalkyl-3-mercaptotriazine With Some Metals", Vysoka Skola Chemickotechonologicka Pardubice, No. 19, pp. 79-84 (1969).
B.V. Rudakov, et al., "Halocyclization of 3-Allylthio-5-Phenyl-1,2,4-Triazine", Russian J. Org. Chem., vol. 33, No. 7, pp. 1033-1036 (1997) (translated from Zhurnal Organicheskoi Khimii, vol. 33, No. 7, pp. 1103-1106 (1997)).
J. Daunis, et al., "Syntheses de triazines-1,2,4-substituees en position 3", Bulletin de la Societe Chimique de France, vol. 10, pp. 3675-3678 (1969).
K.C. Joshi, et al., "Fluorine Containing Bioactive Heterocycles Part III: Synthesis of Some New Fluorine Containing Phenylglyoxals and 1,2,4-Triazine Derivatives", Heterocycles, vol. 16, No. 9, pp. 1545-1553 (1981).
M. Younes et al., "Synthesis of [1,2,4,]Triazolo[3',4':3,4][1,2,4]Triazino[5,6-b]indole Derivatives and 3-Substituted 5-Ethyl-H-1,2,4-trianzino[5,6-b]indole," Archiv Der Pharmazie, Wiley-VCH Verlag GmbH & Co. KGGA, DE, vol. 320, No. 12, pp. 1196-1202 (1987).
J. Larsen, et al., Organic Syntheses, Coll. vol. 9, p. 72 (1998); vol. 72, p. 265 (1995).
L. Carpino, et al., Organic Syntheses, Coll. vol. 5, p. 166 (1973); vol. 44, p. 20 (1964).

* cited by examiner

RUBBER COMPOSITION COMPRISING A THIAZOLINE DERIVATIVE

FIELD OF THE INVENTION

The present invention relates to a rubber composition which can be used in particular in the manufacture of tyres or semi-finished products for tyres, such as treads, the said composition being based on a diene elastomer, on a reinforcing filler and on a vulcanization system comprising a specific thiazoline compound.

RELATED ART

The vulcanization of diene elastomers by sulphur is widely used in the rubber industry, in particular the tyre industry. Use is made, to vulcanize diene elastomers, of a relatively complex vulcanization system comprising, in addition to the sulphur, a primary vulcanization accelerator, such as sulphenamides having a benzothiazole ring system, and also various secondary vulcanization accelerators or vulcanization activators, very particularly zinc derivatives, such as zinc oxide (ZnO), alone or used with fatty acids.

The sulphenamides having a benzothiazole ring system used as primary vulcanization accelerators are, for example, N-cyclohexyl-2-benzothiazolesulphenamide (abbreviated to "CBS"), N,N-dicyclohexyl-2-benzothiazolesulphenamide (abbreviated to "DCBS"), N-tert-butyl-2-benzothiazolesulphenamide (abbreviated to "TBBS") and the mixtures of these compounds.

2-(1,3-Benzothiazol-2-yldithio)-1,3-benzothiazole (abbreviated to "MBTS") is also known as primary vulcanization accelerator.

The rubber compositions must exhibit a sufficient cross-linking while retaining an acceptable compromise between the different rheometric properties.

BRIEF DESCRIPTION OF EMBODIMENTS OF THE INVENTION

In response to this problem, the Applicant Company has discovered a novel rubber composition comprising a thiazoline compound as vulcanization accelerator. This novel rubber composition makes it possible to obtain a composition vulcanized using alternative accelerators to the known accelerators, ideally with a similar compromise in rheometric properties to that obtained with rubber compositions comprising vulcanization accelerators conventionally used.

A subject-matter of the invention is thus a rubber composition for the manufacture of tyres, based on one or more diene elastomers, on one or more reinforcing fillers and on a vulcanization system, the said vulcanization system comprising one or more thiazoline compounds chosen from the compounds of formula

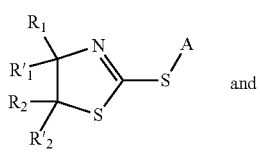

and

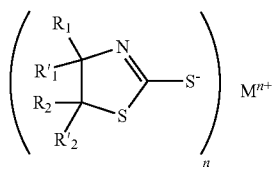

where:

$R_1$, $R_2$, $R'_1$, and $R'_2$ independently represent H or a $C_1$-$C_{25}$ hydrocarbon group chosen from linear, branched or cyclic alkyl groups, aralkyl groups, alkylaryl groups and aryl groups, which are optionally interrupted by one or more heteroatoms, it being possible for $R_1$ to form a non-aromatic ring with $R_2$ or $R'_2$ and it being possible for $R_2$ to form a non-aromatic ring with $R_1$ or $R'_1$, A is chosen from

—H, a group

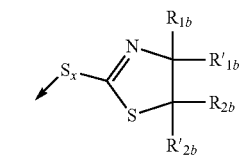

where:

$R_{1b}$ is identical to $R_1$, $R_{2b}$ is identical to $R_2$, $R'_{1b}$ is identical to $R'_1$ and $R'_{2b}$ is identical to $R'_2$, x is an integer greater than or equal to 1, preferably less than or equal to 10, more preferably less than or equal to 8 and very preferably less than or equal to 6, a group

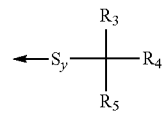

where $R_3$, $R_4$ and $R_5$ independently represent a $C_1$-$C_{18}$ hydrocarbon group which does not comprise a heteroatom, y is an integer greater than or equal to 1, preferably less than or equal to 10, more preferably less than or equal to 8 and very preferably less than or equal to 6, a group

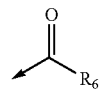

where $R_6$ is a $C_1$-$C_{18}$ hydrocarbon group, optionally interrupted by one or more heteroatoms, provided that $R_1$, $R_2$, $R'_1$ and $R'_2$ do not simultaneously represent H, a group

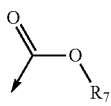

where $R_7$ is a $C_1$-$C_{18}$ hydrocarbon group, optionally interrupted by one or more heteroatoms,
a group

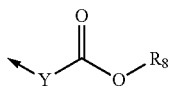

where Y is a $C_1$-$C_{18}$ hydrocarbon chain, optionally interrupted or substituted by one or more heteroatoms;
$R_8$ is a $C_1$-$C_{18}$ hydrocarbon group, optionally interrupted by one or more heteroatoms,
a group

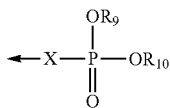

where X is a $C_1$-$C_{18}$ hydrocarbon chain, optionally interrupted or substituted by one or more heteroatoms;
$R_9$ and $R_{10}$ independently represent a $C_1$-$C_{18}$ hydrocarbon group, optionally interrupted by one or more heteroatoms, and
a group

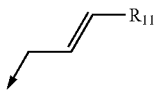

where $R_{11}$ is H or a $C_1$-$C_{18}$ hydrocarbon group, optionally interrupted by one or more heteroatoms,
$M^{n+}$ represents a metal or non-metal cation,
n represents an integer varying between 1 and 4.

In the preceding and succeeding formulae, the arrow (→) denotes the point of attachment of the A and $A_a$ groups to the sulphur atom respectively of the formulae (I) and (I').

Another subject-matter of the invention is a process for preparing a rubber composition for the manufacture of tyres according to the invention, comprising the following stages:
incorporating the reinforcing filler or fillers in the said diene elastomer or elastomers during a first stage, everything being kneaded thermomechanically, in one or more goes, until a maximum temperature of between 110° C. and 190° C. is reached;
subsequently incorporating, during a second stage, the crosslinking system and kneading everything up to a maximum temperature of less than 110° C.

Preferably, the invention relates to the process as defined above in which, between the thermomechanical kneading and the incorporation of the crosslinking system, the combined product is cooled to a temperature of less than or equal to 100° C. Preferably, in this case, the final stage is carried out on a second mixer.

A further subject-matter of the invention is the use of a composition according to the invention in the manufacture of a finished article or of a semi-finished product intended for a motor vehicle ground-contact system, such as a tyre, internal safety support for a tyre, wheel, rubber spring, elastomeric joint, other suspension element and vibration damper. In particular, the composition according to the invention can be used in the manufacture of semi-finished products made of rubber which are intended for tyres, such as treads, crown reinforcing plies, sidewalls, carcass reinforcing plies, beads, protectors, underlayers, rubber blocks and other internal rubbers, in particular decoupling rubbers, intended to provide the bonding or the interface between the abovementioned regions of the tyres.

A further subject-matter of the invention is a finished article or semi-finished product intended for a motor vehicle ground-contact system, in particular tyres and semi-finished products for tyres, in particular treads, comprising a composition according to the invention. The tyres in accordance with the invention are intended in particular for passenger vehicles, two-wheel vehicles as for industrial vehicles chosen from vans, heavy-duty vehicles, i.e. underground, bus, heavy road transport vehicles (lorries, tractors, trailers) or off-road vehicles, heavy agricultural vehicles or earthmoving equipment, planes, and other transportation or handling vehicles.

A further subject-matter of the invention is the use, as vulcanization accelerator in a composition based on one or more diene elastomers, on one or more reinforcing fillers and on a vulcanization system, of one or more thiazoline compounds of formula (I) and/or (II).

Finally, a subject-matter of the invention is a thiazoline of formula

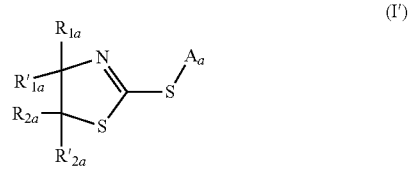

(I')

where:
$R_{1a}$, $R_{2a}$ $R'_{1a}$ and $R'_{2a}$ represent H or a $C_1$-$C_{25}$ hydrocarbon group chosen from linear, branched or cyclic alkyl groups, aralkyl groups, alkylaryl groups and aryl groups, which are optionally interrupted by one or more heteroatoms, it being possible for $R_{1a}$ to form a non-aromatic ring with $R_{2a}$ or $R'_{2a}$ and it being possible for $R_{2a}$ to form a non-aromatic ring with $R_{1a}$ or $R'_{1a}$,
$A_a$ is chosen from
a group

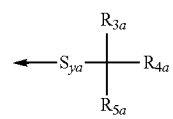

where $R_{3a}$, $R_{4a}$ and $R_{5a}$ independently represent a $C_1$-$C_{18}$ hydrocarbon group, optionally interrupted by one or more heteroatoms,
$y_a$ is an integer greater than or equal to 1, preferably less than or equal to 10, more preferably less than or equal to 8 and very preferably less than or equal to 6, a group

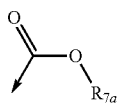

where $R_{7a}$ is a $C_1$-$C_{18}$ hydrocarbon group, optionally interrupted by one or more heteroatoms, a group

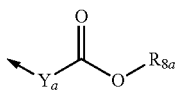

where $Y_a$ is a $C_1$-$C_{18}$ hydrocarbon chain, optionally interrupted or substituted by one or more heteroatoms;

$R_{8a}$ is a $C_1$-$C_{18}$ hydrocarbon group, optionally interrupted by one or more heteroatoms, provided that, if $R_{1a}$, $R_{2a}$, $R'_{1a}$, $R'_{2a}$ simultaneously represent H, $Y_a$ is a $C_1$-$C_{10}$ alkylene chain and $R_{8a}$ is a $C_1$-$C_{10}$ alkyl group.

a group

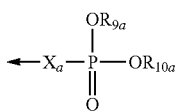

where $X_a$ is a $C_1$-$C_{18}$ hydrocarbon chain, optionally interrupted or substituted by one or more heteroatoms;

$R_{9a}$ and $R_{10a}$ independently represent a $C_1$-$C_{18}$ hydrocarbon group, optionally interrupted by one or more heteroatoms, and a group

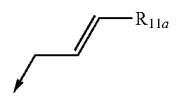

where $R_{11a}$ is H or a $C_1$-$C_{18}$, hydrocarbon group, optionally interrupted by one or more heteroatoms, provided that $R_{1a}$, $R_{2a}$, $R'_{1a}$ and $R'_{2a}$ represent a $C_1$-$C_{18}$ alkyl or $C_3$-$C_{18}$ cycloalkyl group.

DETAILED DESCRIPTION OF EMBODIMENTS OF THE INVENTION

The invention and its advantages will be easily understood in the light of the description and implementational examples which follow.

I. Measurements and Tests

The compounds synthesized as vulcanization accelerators were characterized by mass spectrometry and NMR with the devices and methods indicated below.

Mass Spectrometry

The structural analysis of the expected product and also the determination of the structures of the impurities were carried out by DI/CI analysis (direct introduction in mass spectrometry with chemical ionization as ionization mode).

Operating Conditions:

Reactant gas: methane/ammonia (85/15) at 2 ml/min

Temperature of the source: 200° C.

Mass range swept: 50 at 1000 m/z

NMR

The structural analysis and also the determination of the molar purities of the molecules synthesized are carried out by an NMR analysis. The spectra are acquired on a Bruker Avance 500 MHz spectrometer equipped with a 5 mm BBIz-grade "broad band" probe. The quantitative $^1$H NMR experiment uses a simple 30° pulse sequence and a repetition time of 3 seconds between each of the 64 acquisitions. The $^1$H NMR spectrum coupled with the 2D $^1$H/$^{13}$C HSQC and $^1$H/$^{13}$C HMBC experiments make possible the structural determination of the molecules (cf. tables of assignments). The molar quantifications are carried out from the quantitative 1D $^1$H NMR spectrum.

The rubber compositions in which the thiazoline vulcanization accelerators are tested are characterized, before and after curing, as indicated below.

Rheometry

The measurements are carried out at 150° C. with an oscillating disc rheometer, according to Standard DIN 53529—part 3 (June 1983). The change in the rheometric torque ΔTorque (in dN.m) as a function of time describes the change in the stiffening of the composition as a result of the vulcanization reaction. The measurements are processed according to Standard DIN 53529—part 2 (March 1983) (with the exception of the conversion rate constant): $T_0$ is the induction period, that is to say the time necessary for the start of the vulcanization reaction; $T_\alpha$ (for example $T_{99}$) is the time necessary to achieve a conversion of α %, that is to say α % (for example 99%) of the difference between the minimum and maximum torques.

The conversion rate constant, denoted K (expressed in min$^{-1}$), which is first order, calculated between 30% and 80% conversion, which makes it possible to assess the vulcanization kinetics, is also measured. This constant K is determined by measuring the slope of the rise in torque on the rheogram for curing at 150° C.

II. Conditions for the Implementation of the Invention

As explained above, the composition according to the invention is based on one or more diene elastomers, on one or more reinforcing fillers and on a vulcanization system.

The expression composition "based on" should be understood as meaning a composition comprising the mixture and/or the reaction product of the various constituents used, some of these base constituents being capable of reacting or intended to react with one another, at least in part, during the various phases of manufacture of the composition, in particular during the vulcanization thereof.

In the present description, unless expressly indicated otherwise, all the percentages (%) are % by weight. Furthermore, any interval of values denoted by the expression "between a and b" represents the range of values extending from more than a to less than b (that is to say, limits a and b excluded), whereas any interval of values denoted by the expression "from a to b" means the range of values extending from a up to b (that is to say, including the strict limits a and b).

II-1. Diene Elastomer

A "diene" elastomer or rubber should be understood, in a known way, as meaning an elastomer resulting at least in part (i.e., a homopolymer or a copolymer) from diene monomers (monomers carrying two conjugated or non-conjugated carbon-carbon double bonds).

These diene elastomers can be classified into two categories: "essentially unsaturated" or "essentially saturated". Generally, "essentially unsaturated" is understood to mean a diene elastomer resulting at least in part from conjugated diene monomers having a content of units of diene origin (conjugated dienes) which is greater than 15% (mol %); thus it is that diene elastomers, such as butyl rubbers or copolymers of dienes and α-olefins of EPDM type, do not come within the preceding definition and can in particular be described as "essentially saturated" diene elastomers (low or very low content, always less than 15%, of units of diene origin). In the category of "essentially unsaturated" diene elastomers, "highly unsaturated" diene elastomer is understood to mean in particular a diene elastomer having a content of units of diene origin (conjugated dienes) which is greater than 50%.

Given these definitions, diene elastomer capable of being used in the compositions in accordance with the invention is understood more particularly to mean:

(a)—any homopolymer obtained by polymerization of a conjugated diene monomer having from 4 to 12 carbon atoms;

(b)—any copolymer obtained by copolymerization of one or more conjugated dienes with one another or with one or more vinylaromatic compounds having from 8 to 20 carbon atoms;

(c)—a ternary copolymer obtained by copolymerization of ethylene and of an α-olefin having from 3 to 6 carbon atoms with a non-conjugated diene monomer having from 6 to 12 carbon atoms, such as, for example, the elastomers obtained from ethylene and propylene with a non-conjugated diene monomer of the abovementioned type, such as, in particular, 1,4-hexadiene, ethylidenenorbornene or dicyclopentadiene;

(d)—a copolymer of isobutene and of isoprene (butyl rubber) and also the halogenated versions, in particular chlorinated or brominated versions, of this type of copolymer.

Although it applies to any type of diene elastomer, a person skilled in the art of tyres will understand that the present invention is preferably employed with essentially unsaturated diene elastomers, in particular of the above type (a) or (b).

The following are suitable in particular as conjugated dienes: 1,3-butadiene, 2-methyl-1,3-butadiene, 2,3-di($C_1$-$C_5$alkyl)-1,3-butadienes, such as, for example, 2,3-dimethyl-1,3-butadiene, 2,3-diethyl-1,3-butadiene, 2-methyl-3-ethyl-1,3-butadiene or 2-methyl-3-isopropyl-1,3-butadiene, an aryl-1,3-butadiene, 1,3-pentadiene or 2,4-hexadiene. The following, for example, are suitable as vinylaromatic compounds: styrene, ortho-, meta- or para-methylstyrene, the "vinyltoluene" commercial mixture, para-(tert-butyl)styrene, methoxystyrenes, chlorostyrenes, vinylmesitylene, divinylbenzene or vinylnaphthalene.

The copolymers can comprise between 99% and 20% by weight of diene units and between 1% and 80% by weight of vinylaromatic units. The elastomers can have any microstructure, which depends on the polymerization conditions used, in particular on the presence or absence of a modifying and/or randomizing agent and on the amounts of modifying and/or randomizing agent employed. The elastomers can, for example, be block, statistical, sequential or microsequential elastomers and can be prepared in dispersion, in emulsion or in solution; they can be coupled and/or star-branched or else functionalized with a coupling and/or star-branching or functionalization agent. Mention may be made, for example, for coupling to carbon black, of functional groups comprising a C—Sn bond or aminated functional groups, such as aminobenzophenone, for example; mention may be made, for example, for coupling to a reinforcing inorganic filler, such as silica, of silanol or polysiloxane functional groups having a silanol end (such as described, for example, in FR 2 740 778, U.S. Pat. No. 6,013,718 or WO 2008/141702), alkoxysilane groups (such as described, for example, in FR 2 765 882 or U.S. Pat. No. 5,977,238), carboxyl groups (such as described, for example, in WO 01/92402 or U.S. Pat. No. 6,815,473, WO 2004/096865 or US 2006/0089445) or else polyether groups (such as described, for example, in EP 1 127 909, U.S. Pat. No. 6,503,973, WO 2009/000750 or WO 2009/000752). Mention may also be made, as other examples of functionalized elastomers, of elastomers (such as SBR, BR, NR or IR) of the epoxidized type.

The following are suitable: polybutadienes and in particular those having a content (mol %) of 1,2- units of between 4% and 80% or those having a content (mol %) of cis-1,4- units of greater than 80%, polyisoprenes, butadiene/styrene copolymers and in particular those having a Tg (glass transition temperature, measured according to ASTM D3418) of between 0° C. and −70° C. and more particularly between −10° C. and −60° C., a styrene content of between 5% and 60% by weight and more particularly between 20% and 50%, a content (mol %) of 1,2- bonds of the butadiene part of between 4% and 75% and a content (mol %) of trans-1,4- bonds of between 10% and 80%, butadiene/isoprene copolymers and especially those having an isoprene content of between 5% and 90% by weight and a Tg of −40° C. to −80° C., or isoprene/styrene copolymers and especially those having a styrene content of between 5% and 50% by weight and a Tg of between 5° C. and −50° C. In the case of butadiene/styrene/isoprene copolymers, those having a styrene content of between 5% and 50% by weight and more particularly of between 10% and 40%, an isoprene content of between 15% and 60% by weight and more particularly of between 20% and 50%, a butadiene content of between 5% and 50% by weight and more particularly of between 20% and 40%, a content (mol %) of 1,2- units of the butadiene part of between 4% and 85%, a content (mol %) of trans-1,4- units of the butadiene part of between 6% and 80%, a content (mol %) of 1,2- plus 3,4- units of the isoprene part of between 5% and 70% and a content (mol %) of trans-1,4- units of the isoprene part of between 10% and 50%, and more generally any butadiene/styrene/isoprene copolymer having a Tg of between −5° C. and −70° C., are suitable in particular.

To summarize, the diene elastomer or elastomers of the composition according to the invention are preferably selected from the group of highly unsaturated diene elastomers consisting of polybutadienes (abbreviated to "BRs"), synthetic polyisoprenes (IRs), natural rubber (NR), butadiene copolymers, isoprene copolymers and the mixtures of these elastomers. Such copolymers are more preferably selected from the group consisting of butadiene/styrene copolymers (SBRs), isoprene/butadiene copolymers (BIRs), isoprene/styrene copolymers (SIRs) and isoprene/butadiene/styrene copolymers (SBIRs).

According to one embodiment, the diene elastomer is natural rubber.

According to another specific embodiment, the diene elastomer is predominantly (i.e., for more than 50 phr) an SBR, whether an SBR prepared in emulsion ("ESBR") or an SBR prepared in solution ("SSBR"), or an SBR/BR, SBR/NR (or SBR/IR), BR/NR (or BR/IR) or also SBR/BR/NR (or SBR/BR/IR) blend (mixture). In the case of an SBR (ESBR or SSBR) elastomer, use is made in particular of an SBR having a moderate styrene content, for example of between 20% and 35% by weight, or a high styrene content, for example from 35% to 45%, a content of vinyl bonds of the butadiene part of between 15% and 70%, a content (mol %) of trans-1,4- bonds of between 15% and 75% and a Tg of between −10° C. and −55° C.; such an SBR can advantageously be used as a mixture with a BR preferably having more than 90% (mol %) of cis-1,4- bonds.

According to another specific embodiment, the diene elastomer is predominantly (for more than 50 phr) an isoprene elastomer. This is in particular the case when the compositions of the invention are intended to constitute, in the tyres, rubber matrices of certain treads (for example for industrial vehicles), of crown reinforcing plies (for example of working plies, protection plies or hooping plies), of carcass reinforcing plies, of sidewalls, of beads, of protectors, of underlayers, of rubber blocks and other internal rubbers providing the interface between the abovementioned regions of the tyres.

"Isoprene elastomer" is understood to mean, in a known way, an isoprene homopolymer or copolymer, in other words a diene elastomer selected from the group consisting of natural rubber (NR), synthetic polyisoprenes (IRs), various isoprene copolymers and the mixtures of these elastomers. Mention will in particular be made, among isoprene copolymers, of isobutene/isoprene (butyl rubber—IIR), isoprene/styrene (SIR), isoprene/butadiene (BIR) or isoprene/butadiene/styrene (SBIR) copolymers. This isoprene elastomer is preferably natural rubber or a synthetic cis-1,4-polyisoprene; use is preferably made, among these synthetic polyisoprenes, of polyisoprenes having a content (mol %) of cis-1,4-bonds of greater than 90%, more preferably still of greater than 98%.

According to another specific embodiment, in particular when it is intended for a tyre sidewall or for an airtight internal rubber of a tubeless tyre (or other air-impermeable component), the composition in accordance with the invention can comprise at least one essentially saturated diene elastomer, in particular at least one EPDM copolymer or one butyl rubber (optionally chlorinated or brominated), whether these copolymers are used alone or as a mixture with highly unsaturated diene elastomers as mentioned above, in particular NR or IRs, BR or SBRs.

According to another preferred embodiment of the invention, the rubber composition comprises a blend of a (one or more) "high Tg" diene elastomer exhibiting a Tg of between −70° C. and 0° C. and of a (one or more) "low Tg" diene elastomer of between −110° C. and −80° C., more particularly between −105° C. and −90° C. The high Tg elastomer is preferably selected from the group consisting of S-SBRs, E-SBRs, natural rubber, synthetic polyisoprenes (exhibiting a content (mol %) of cis-1,4- enchainments preferably of greater than 95%), BIRs, SIRs, SBIRs, and the mixtures of these elastomers. The low Tg elastomer preferably comprises butadiene units according to a content (mol %) at least equal to 70%; it preferably consists of a polybutadiene (BR) exhibiting a content (mol %) of cis-1,4- enchainments of greater than 90%.

According to another specific embodiment of the invention, the rubber composition comprises, for example, from 30 to 100 phr, in particular from 50 to 100 phr, of a high Tg elastomer as a blend with from 0 to 70 phr, in particular from 0 to 50 phr, of a low Tg elastomer; according to another example, it comprises, for the totality of the 100 phr, one or more SBRs prepared in solution.

According to another specific embodiment of the invention, the diene elastomer of the composition according to the invention comprises a blend of a BR (as low Tg elastomer) exhibiting a content (mol %) of cis-1,4- enchainments of greater than 90% with one or more S-SBRs or E-SBRs (as high Tg elastomer(s)).

The composition according to the invention can comprise just one diene elastomer or a mixture of several diene elastomers, it being possible for the diene elastomer or elastomers to be used in combination with any type of synthetic elastomer other than a diene elastomer, indeed even with polymers other than elastomers, for example thermoplastic polymers.

II-2. Reinforcing Filler

Use may be made of any type of reinforcing filler known for its abilities to reinforce a rubber composition which can be used for the manufacture of tyres, for example an organic filler, such as carbon black, a reinforcing inorganic filler, such as silica, or also a blend of these two types of filler, in particular a blend of carbon black and silica.

All carbon blacks, in particular blacks of the HAF, ISAF or SAF type, conventionally used in tyres ("tyre-grade" blacks), are suitable as carbon blacks. Mention will more particularly be made, among the latter, of the reinforcing carbon blacks of the 100, 200 or 300 series (ASTM grades), such as, for example, the N115, N134, N234, N326, N330, N339, N347 or N375 blacks, or else, depending on the applications targeted, the blacks of higher series (for example N660, N683 or N772). The carbon blacks might, for example, be already incorporated in the isoprene elastomer in the form of a masterbatch (see, for example, Applications WO 97/36724 or WO 99/16600).

Mention may be made, as examples of organic fillers other than carbon blacks, of functionalized polyvinylaromatic organic fillers, such as described in Applications WO-A-2006/069792 and WO-A-2006/069793.

The term "reinforcing inorganic filler" should be understood, in the present patent application, by definition, as meaning any inorganic or mineral filler, whatever its colour and its origin (natural or synthetic), also known as "white filler", "clear filler" or indeed even "non-black filler", in contrast to carbon black, capable of reinforcing by itself alone, without means other than an intermediate coupling agent, a rubber composition intended for the manufacture of tyres, in other words capable of replacing, in its reinforcing role, a conventional tyre-grade carbon black; such a filler is generally characterized, in a known way, by the presence of hydroxyl (—OH) groups at its surface.

The physical state under which the reinforcing inorganic filler is provided is not important, whether it is in the form of a powder, of microbeads, of granules, of beads or any other appropriate densified form. Of course, the term "reinforcing inorganic filler" is also understood to mean mixtures of different reinforcing inorganic fillers, in particular of highly dispersible siliceous and/or aluminous fillers as described below.

Mineral fillers of the siliceous type, in particular silica ($SiO_2$), or of the aluminous type, in particular alumina ($Al_2O_3$), are suitable in particular as reinforcing inorganic fillers. The silica used can be any reinforcing silica known to a person skilled in the art, in particular any precipitated or fumed silica exhibiting a BET specific surface and a CTAB specific surface both of less than 450 $m^2/g$, preferably from 30 to 400 $m^2/g$. Mention will be made, as highly dispersible precipitated silicas ("HDSs"), for example, of the Ultrasil 7000 and Ultrasil 7005 silicas from Degussa, the Zeosil 1165 MP, 1135 MP and 1115 MP silicas from Rhodia, the Hi-Sil EZ150G silica from PPG, the Zeopol 8715, 8745 and 8755 silicas from Huber or the silicas with a high specific surface as described in Application WO 03/16837.

When the composition according to the invention is intended for tyre treads having a low rolling resistance, the reinforcing inorganic filler used, in particular if it is silica, preferably has a BET specific surface of between 45 and 400 m²/g, more preferably of between 60 and 300 m²/g.

Preferably, the content of total reinforcing filler (carbon black and/or reinforcing inorganic filler, such as silica) is between 20 and 200 phr, more preferably between 30 and 150 phr, the optimum being, in a known way, different depending on the specific applications targeted: the level of reinforcement expected with regard to a bicycle tyre, for example, is, of course, less than that required with regard to a tyre capable of running at high speed in a sustained manner, for example a motorcycle tyre, a tyre for a passenger vehicle or a tyre for a utility vehicle, such as a heavy-duty vehicle.

According to one embodiment of the invention, use is made of a reinforcing filler comprising between 30 and 150 phr, more preferably between 50 and 120 phr, of inorganic filler, particularly of silica and optionally of carbon black; the carbon black, when it is present, is preferably used at a content of less then 20 phr, more preferably of less than 10 phr (for example between 0.1 and 10 phr).

According to another embodiment, the reinforcing filler is carbon black.

Use is made, in a known way, in order to couple the reinforcing inorganic filler to the diene elastomer, of an at least bifunctional coupling agent (or bonding agent) intended to provide a satisfactory connection, of chemical and/or physical nature, between the inorganic filler (surface of its particles) and the diene elastomer, in particular bifunctional organosilanes or polyorganosiloxanes.

Use is made in particular of silane polysulphides, referred to as "symmetrical" or "unsymmetrical" depending on their specific structure, such as described, for example, in Applications WO 03/002648 (or US 2005/016651) and WO 03/002649 (or US 2005/016650).

Suitable in particular, without the definition below being limiting, are silane polysulphides referred to as "symmetrical", corresponding to the following general formula (III):

$$Z\text{-}D\text{-}S_p\text{-}D\text{-}Z, \quad (III)$$

in which:
p is an integer from 2 to 8 (preferably from 2 to 5);
D is a divalent hydrocarbon radical (preferably $C_1$-$C_{18}$ alkylene groups or $C_6$-$C_{12}$ arylene groups, more particularly $C_1$-$C_{10}$ alkylenes, in particular $C_1$-$C_4$ alkylenes, especially propylene);
Z corresponds to one of the formulae below:

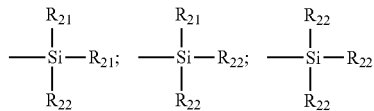

in which:
the $R_{21}$ radicals, which are substituted or unsubstituted and identical to or different from one another, represent a $C_1$-$C_{18}$ alkyl, $C_5$-$C_{18}$ cycloalkyl or $C_6$-$C_{18}$ aryl group (preferably $C_1$-$C_6$ alkyl, cyclohexyl or phenyl groups, in particular $C_1$-$C_4$ alkyl groups, more particularly methyl and/or ethyl);
the $R_{22}$ radicals, which are substituted or unsubstituted and identical to or different from one another, represent a $C_1$-$C_{18}$ alkoxyl or $C_5$-$C_{18}$ cycloalkoxyl group (preferably a group chosen from $C_1$-$C_8$ alkoxyls and $C_5$-$C_8$ cycloalkoxyls, more particularly still a group chosen from $C_1$-$C_4$ alkoxyls, in particular methoxyl and ethoxyl).

In the case of a mixture of alkoxysilane polysulphides corresponding to the above formula (III), in particular normal commercially available mixtures, the mean value of the "p" indices is a fractional number preferably of between 2 and 5, more preferably of approximately 4. However, the invention can also advantageously be carried out, for example, with alkoxysilane disulphides (p=2).

Mention will more particularly be made, as examples of silane polysulphides, of bis(($C_1$-$C_4$)alkoxyl($C_1$-$C_4$)alkylsilyl($C_1$-$C_4$)alkyl)polysulphides (in particular disulphides, trisulphides or tetrasulphides), such as, for example, bis(3-trimethoxysilylpropyl) or bis(3-triethoxysilylpropyl)polysulphides. Use will in particular be made, among these compounds, of bis(3-triethoxysilylpropyl)tetrasulphide, abbreviated to TESPT, of formula $[(C_2H_5O)_3Si(CH_2)_3S_2]_2$, or of bis(triethoxysilylpropyl)disulphide, abbreviated to TESPD, of formula $[(C_2H_5O)_3Si(CH_2)_3S]_2$. Mention will also be made, as preferred examples, of bis(mono($C_1$-$C_4$)alkoxyldi($C_1$-$C_4$)alkylsilylpropyl)polysulphides (in particular disulphides, trisulphides or tetrasulphides), more particularly bis(monoethoxydimethylsilylpropyl)tetrasulphide, such as described in Patent Application WO 02/083782 (or US 2004/132880).

Mention will in particular be made, as coupling agents other than an alkoxysilane polysulphide, of bifunctional POSs (polyorganosiloxanes) or else of hydroxysilane polysulphides ($R_{22}$=OH in the above formula III), such as described in Patent Applications WO 02/30939 (or U.S. Pat. No. 6,774,255) and WO 02/31041 (or US 2004/051210), or else of silanes or POSs bearing azodicarbonyl functional groups, such as described, for example, in Patent Applications WO 2006/125532, WO 2006/125533 or WO 2006/125534.

In the rubber compositions in accordance with the invention, the content of coupling agent is preferably between 4 and 12 phr, more preferably between 3 and 8 phr.

A person skilled in the art will understand that a reinforcing filler of another nature, in particular organic nature, might be used as filler equivalent to the reinforcing inorganic filler described in the present section, provided that this reinforcing filler is covered with an inorganic layer, such as silica, or else comprises, at its surface, functional sites, in particular hydroxyls, requiring the use of a coupling agent in order to form the connection between the filler and the elastomer.

II.3 Vulcanization System

The vulcanization system proper is based on sulphur (or on a sulphur-donating agent) and on a primary vulcanization accelerator. Additional to this base vulcanization system are various known secondary vulcanization accelerators or vulcanization activators, such as zinc oxide, stearic acid or equivalent compounds, or guanidine derivatives (in particular diphenylguanidine), incorporated during the first non-productive phase and/or during the productive phase, as described subsequently.

The sulphur is used at a preferred content of between 0.5 and 10 phr, more preferably of between 0.5 and 5 phr, in particular between 0.5 and 3 phr, when the composition of the invention is intended, according to a preferred form of the invention, to constitute a tyre tread.

The primary vulcanization accelerator must make possible crosslinking of the rubber compositions within industrially acceptable times, while retaining a minimum safe time ("scorch time") during which the compositions can be shaped without risk of premature vulcanization ("scorching").

According to the invention, the vulcanization system comprises, as primary vulcanization accelerator, one or more thiazoline compounds chosen from the compounds of formula

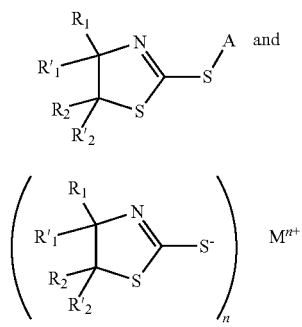

where:

$R_1$, $R_2$, $R'_1$, and $R'_2$ independently represent H or a $C_1$-$C_{25}$ hydrocarbon group chosen from linear, branched or cyclic alkyl groups, aralkyl groups, alkylaryl groups and aryl groups, which are optionally interrupted by one or more heteroatoms, it being possible for $R_1$ to form a non-aromatic ring with $R_2$ or $R'_2$ and it being possible for $R_2$ to form a non-aromatic ring with $R_1$ or $R'_1$, A is chosen from

—H, a group

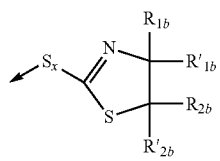

where:

$R_{1b}$ is identical to $R_1$, $R_{2b}$ is identical to $R_2$, $R'_{1b}$ is identical to $R'_1$ and $R'_{2b}$ is identical to $R'_2$, x is an integer greater than or equal to 1, preferably less than or equal to 10, more preferably less than or equal to 8 and very preferably less than or equal to 6, a group

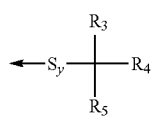

where $R_3$, $R_4$ and $R_5$ independently represent a $C_1$-$C_{18}$ hydrocarbon group which does not comprise a heteroatom, y is an integer greater than or equal to 1, preferably less than or equal to 10, more preferably less than or equal to 8 and very preferably less than or equal to 6, a group

where $R_6$ is a $C_1$-$C_{18}$ hydrocarbon group, optionally interrupted by one or more heteroatoms, provided that $R_1$, $R_2$, $R'_1$ and $R'_2$ do not simultaneously represent H, a group

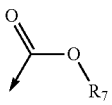

where $R_7$ is a $C_1$-$C_{18}$ hydrocarbon group, optionally interrupted by one or more heteroatoms, a group

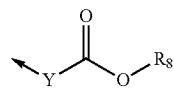

where Y is a $C_1$-$C_{18}$ hydrocarbon chain, optionally interrupted or substituted by one or more heteroatoms;

$R_8$ is a $C_1$-$C_{18}$ hydrocarbon group, optionally interrupted by one or more heteroatoms, a group

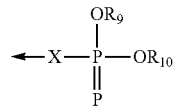

where X is a $C_1$-$C_{18}$ hydrocarbon chain, optionally interrupted or substituted by one or more heteroatoms;

$R_9$ and $R_{10}$ independently represent a $C_1$-$C_{18}$ hydrocarbon group, optionally interrupted by one or more heteroatoms, and a group

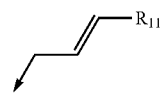

where $R_{11}$ is H or a $C_1$-$C_{18}$ hydrocarbon group, optionally interrupted by one or more heteroatoms, $M^{n+}$ represents a metal or non-metal cation, n represents an integer varying between 1 and 4.

The compounds of formula (I) and (II) can advantageously replace, in all or part, the accelerator compounds conventionally used.

Cyclic alkyl group is understood to mean an alkyl group composed of one or more rings.

Hydrocarbon group or chain interrupted by one or more heteroatoms is understood to mean a group or chain comprising one or more heteroatoms, each heteroatom being between two carbon atoms of the said group or the said chain or between a carbon atom of the said group or the said chain and another heteroatom of the said group or the said chain or between two other heteroatoms of the said group or the said chain.

The heteroatom or heteroatoms can be a nitrogen, sulphur or oxygen atom.

According to a first embodiment, $R_1$, $R_2$, $R'_1$, and $R'_2$ independently represent H or a methyl group.

According to a second embodiment, $R_1$, $R_2$, $R'_1$, and $R'_2$ represent each H.

According to a third embodiment, two radicals chosen from $R_1$, $R_2$, $R'_1$, and $R'_2$ represent a methyl group, the other two representing H.

The compound or compounds of formula (I) are advantageously chosen from the compounds for which the A group is a group

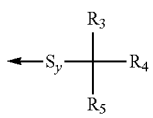

where y and $R_3$ to $R_5$ are as defined above.

The $R_3$ to $R_{11}$ groups can be independently chosen from linear, branched or cyclic alkyl groups, aryl groups, aralkyl groups and alkylaryl groups, with the proviso of optional conditions clarified above for each of these groups.

The X and Y groups can be independently chosen from linear, branched or cyclic alkylene groups, arylene groups and alkylarylene groups.

The $M^{n+}$ cation can be a metal cation chosen from $Zn^{2+}$, $Cu^{2+}$, $Na^+$, $K^+$ and $Li^+$.

The $M^{n+}$ cation can be a non-metal cation, such as an ammonium ion, for example the $NMe_4^+$, $NH_4^+$ or $H_3NMe^+$ ion.

According to a specific embodiment, $R_3$, $R_4$ and $R_5$ represent a methyl group.

According to a specific embodiment, $R_6$ represents a $C_1$-$C_4$ alkyl, more preferably a $C_1$-$C_3$ alkyl and very preferably a methyl group or an ethyl group.

According to a specific embodiment, $R_7$ represents a $C_1$-$C_4$ alkyl, more preferably a $C_1$-$C_3$ alkyl and very preferably a methyl group or an ethyl group, or else $R_7$ represents an aralkyl group, such as, for example, a benzyl group.

According to a specific embodiment, Y represents a $C_1$-$C_4$ alkylene, more preferably a $C_1$-$C_3$ alkylene and very preferably a propylene group or an ethylene group and $R_8$ represents a $C_1$-$C_4$ alkyl, more preferably a $C_1$-$C_3$ alkyl and very preferably a methyl group or an ethyl group.

According to a specific embodiment, X represents a $C_1$-$C_4$ alkylene, more preferably a $C_1$-$C_3$ alkylene and very preferably a methylene group or an ethylene group and $R_9$ and $R_{10}$ independently represent a $C_1$-$C_4$ alkyl, more preferably a $C_1$-$C_3$ alkyl and very preferably a methyl group or an ethyl group.

According to a specific embodiment, $R_{11}$ represents H.

Mention may be made, as specific compounds of formula (I), of the following compounds:

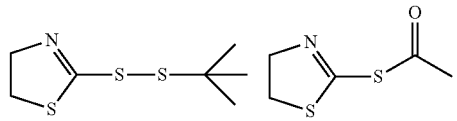

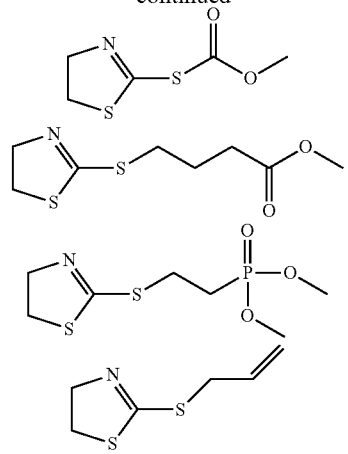

The compound or compounds of formula (I) and/or (II) generally represent from 0.1 to 7 phr, preferably from 0.2 to 7 phr, more preferably from 0.5 to 7 phr and better still from 0.5 to 5 phr.

The vulcanization system of the composition according to the invention can also comprise one or more additional primary accelerators, in particular compounds of the family of the thiurams, zinc dithiocarbamate derivatives, sulphenamides, guanidines or thiophosphates.

II-4. Various Additives

The rubber composition according to the invention can also comprise all or a portion of the usual additives generally used in elastomer compositions intended for the manufacture of tyres, in particular of treads, such as, for example, plasticizers or extending oils, whether the latter are of aromatic or non-aromatic nature, pigments, protection agents, such as anti-ozone waxes (such as Cire Ozone C32 ST), chemical anti-ozonants or antioxidants (such as 6-PPD), anti-fatigue agents, reinforcing resins, methylene acceptors (for example, phenolic novolak resin) or methylene donors (for example, HMT or H3M), as described, for example, in Application WO 02/10269.

Preferably, the composition according to the invention comprises, as preferred non-aromatic or very weakly aromatic plasticizing agent, at least one compound selected from the group consisting of naphthenic oils, paraffinic oils, MES oils, TDAE oils, glycerol esters (in particular trioleates), plasticizing hydrocarbon resins exhibiting a high Tg preferably of greater than 30° C., and mixtures of such compounds.

The composition according to the invention can also comprise, in addition to the coupling agents, activators of the coupling of the reinforcing inorganic filler or more generally processing aids capable, in a known way, by virtue of an improvement in the dispersion of the inorganic filler in the rubber matrix and of a lowering in the viscosity of the compositions, of improving their ease of processing in the raw state, these processing aids being, for example, hydrolysable silanes, such as alkylalkoxysilanes (in particular alkyltriethoxysilanes), polyols, polyethers (for example, polyethylene glycols), primary, secondary or tertiary amines (for example, trialkanolamines), hydroxylated or hydrolysable POSs, for example α,ω-dihydroxypolyorganosiloxanes (in particular α,ω-dihydroxypolydimethylsiloxanes), or fatty acids, such as, for example, stearic acid.

II-5. Manufacture of the Rubber Compositions

The rubber composition according to the invention is manufactured in appropriate mixers, generally using two successive phases of preparation according to a general procedure well known to a person skilled in the art: a first phase of thermomechanical working or kneading (sometimes referred to as "non-productive" phase) at high temperature, up to a maximum temperature of between 110° C. and 190° C., preferably between 115° C. and 150° C. and more preferably still between 115° C. and 140° C., followed by a second phase of mechanical working (sometimes referred to as "productive" phase) at lower temperature, typically below 110° C., for example between 40° C. and 100° C., during which finishing phase the crosslinking or vulcanization system can be incorporated.

According to a preferred embodiment of the invention, all the base constituents of the composition of the invention, with the exception of the vulcanization system, namely the reinforcing filler or fillers and the coupling agent, if appropriate, are intimately incorporated, by kneading, in the diene elastomer or in the diene elastomers during the first "non-productive" phase, that is to say that at least these various base constituents are introduced into the mixer and are thermomechanically kneaded, in one or more stages, until the maximum temperature of between 110° C. and 190° C., preferably of between 115° C. and 150° C., is reached.

The two phases can be carried out consecutively on one and the same mixer or can be separated by a stage of cooling to a temperature of less than 100° C., the final stage then being carried out on a second mixer.

By way of example, the first (non-productive) phase is carried out in a single thermomechanical stage during which all the necessary constituents, the optional supplementary processing aids and various other additives, with the exception of the vulcanization system, are introduced into an appropriate mixer, such as an ordinary internal mixer. The total duration of the kneading, in this non-productive phase, is preferably between 1 and 15 min. After cooling the mixture thus obtained during the first non-productive phase, the vulcanization system is then incorporated at low temperature, generally in an external mixer, such as an open mill; everything is then mixed (productive phase) for a few minutes, for example between 2 and 15 min.

The final composition thus obtained is subsequently calendered, for example in the form of a sheet or plaque, in particular for laboratory characterization, or else extruded in the form of a rubber profiled element which can be used, for example, as a tyre tread for a passenger vehicle.

II-6. Specific Thiazoline Compounds

A further subject-matter of the invention is a thiazoline compound of formula

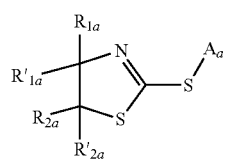

(I')

where:

$R_{1a}$, $R_{2a}$, $R'_{1a}$ and $R'_{2a}$ represent H or a $C_1$-$C_{25}$ hydrocarbon group chosen from linear, branched or cyclic alkyl groups, aralkyl groups, alkylaryl groups and aryl groups, which are optionally interrupted by one or more heteroatoms, it being possible for $R_{1a}$ to form a non-aromatic ring with $R_{2a}$ or $R'_{2a}$ and it being possible for $R_{2a}$ to form a non-aromatic ring with $R_{1a}$ or $R'_{1a}$, $A_a$ is chosen from
    a group

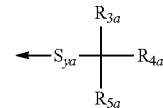

where $R_{1a}$, $R_{4a}$ and $R_{5a}$ independently represent a $C_1$-$C_{18}$ hydrocarbon group, optionally interrupted by one or more heteroatoms, $y_a$ is an integer greater than or equal to 1, preferably less than or equal to 10, more preferably less than or equal to 8 and very preferably less than or equal to 6, a group

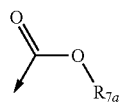

where $R_{7a}$ is a $C_1$-$C_{18}$ hydrocarbon group, optionally interrupted by one or more heteroatoms,

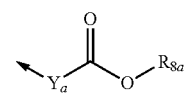

where $Y_a$ is a $C_1$-$C_{18}$ hydrocarbon chain, optionally interrupted or substituted by one or more heteroatoms;

$R_{8a}$ is a $C_1$-$C_{18}$ hydrocarbon group, optionally interrupted by one or more heteroatoms, provided that, if $R_{1a}$, $R_{2a}$, $R'_{1a}$ and $R'_{2a}$ simultaneously represent H, $Y_a$ is an $C_1$-$C_{10}$ alkylene chain and $R_{8a}$ is a $C_1$-$C_{10}$ alkyl group, a group

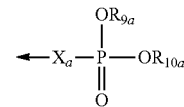

where $X_a$ is a $C_1$-$C_{18}$ hydrocarbon chain, optionally interrupted or substituted by one or more heteroatoms;

$R_{9a}$ and $R_{10a}$ independently represent a $C_1$-$C_{18}$ hydrocarbon group, optionally interrupted by one or more heteroatoms, and a group

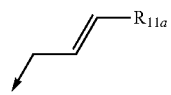

Where $R_{11a}$ is H or an $C_1$-$C_{18}$ hydrocarbon group, optionally interrupted by one or more heteroatoms, provided that $R_{1a}$, $R_{2a}$, $R'_{1a}$ and $R'_{2a}$ represent a $C_1$-$C_{18}$ alkyl or $C_3$-$C_{18}$ cycloalkyl group Cyclic alkyl group is understood to mean an alkyl group composed of one or more rings.

Hydrocarbon group or chain interrupted by one or more heteroatoms is understood to mean a group or chain comprising one or more heteroatoms, each heteroatom being between two carbon atoms of the said group or the said chain or between a carbon atom of the said group or the said chain and another heteroatom of the said group or the said chain or between two other heteroatoms of the said group or the said chain.

The heteroatom or heteroatoms can be a nitrogen, sulphur or oxygen atom.

According to a first embodiment, $R_{1a}$, $R_{2a}$, $R'_{1a}$ and $R'_{2a}$ independently represent H or a methyl group.

According to a second embodiment, $R_{1a}$, $R_{2a}$, $R'_{1a}$ and $R'_{2a}$ each represent H.

According to a third embodiment, two radicals chosen from $R_{1a}$, $R_{2a}$, $R'_{1a}$ and $R'_{2a}$ represent a methyl group, the other two representing H.

Advantageously, the thiazoline compound of formula (I') is such that $A_a$ is a group

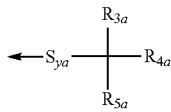

where $y_a$ and $R_{3a}$ to $R_{5a}$ are as defined above.

The $R_{3a}$ to $R_{5a}$ and $R_{7a}$ to $R_{11a}$ groups can be independently chosen from linear, branched or cyclic alkyl groups, aryl groups, aralkyl groups and alkylaryl groups, with the proviso of optional conditions clarified above for each of these groups.

The $X_a$ and $Y_a$ groups can be independently chosen from linear, branched or cyclic alkylene groups, arylene groups and alkylarylene groups.

According to a specific embodiment, $R_{3a}$, $R_{4a}$ and $R_{5a}$ represent a methyl group.

According to a specific embodiment, $R_{7a}$ represents a $C_1$-$C_4$ alkyl, more preferably a $C_1$-$C_3$ alkyl and very preferably a methyl group or an ethyl group, or else $R_{7a}$ represents an aralkyl group, such as, for example, a benzyl group.

According to a specific embodiment, $Y_a$ represents a $C_1$-$C_4$ alkylene, more preferably a $C_1$-$C_3$ alkylene and very preferably a propylene group or an ethylene group and $R_{8a}$ represents a $C_1$-$C_4$ alkyl, more preferably a $C_1$-$C_3$ alkyl and very preferably a methyl group or an ethyl group.

According to a specific embodiment, $X_a$ represents a $C_1$-$C_4$ alkylene, more preferably a $C_1$-$C_3$ alkylene and very preferably a methylene group or an ethylene group and $R_{9a}$ and $R_{10a}$ independently represent a $C_1$-$C_4$ alkyl, more preferably a $C_1$-$C_3$ alkyl and very preferably a methyl group or an ethyl group.

According to a specific embodiment, $R_{11a}$ represents H.

II-7. Preparation of the Accelerators of General Formula (I), (II) and (I')

A person skilled in the art knows how to prepare the thiazoline compounds of general formula (I) when the A group represents a hydrogen atom, in which case the thiazolines are substituted by a thiol. This thiol can be salified by techniques known to a person skilled in the art in order to obtain the thiolate compounds of general formula (II).

A person skilled in the art, starting from the thiols or thiolates described above and depending on the nature of the A group, can obtain the compounds of general formula (I) or (I') as described below:

When the A radical represents a group

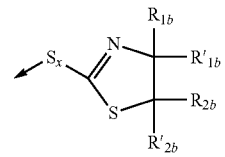

as defined above, the compound can be prepared by an oxidative coupling.

An organic or inorganic oxidizing agent (for example diisopropyl azodicarboxylate or ammonium persulphate, or also iodine or a sodium hypochlorite solution) is added to a solution of the thiol precursor. For example, this type of procedure is described in the following documents:
with NaOCl by Mathes in U.S. Pat. No. 2,196,607 (1940),
with $(NH_4)_2S_2O_8$ in Stewart, Mathes, J. of Org. Chem., 1949, vol. 14, pp. 1111-1117.

By this reaction, the derivatives in which x=1 are obtained. In order to obtain the compounds in which x is greater than 1, it is possible to insert sulphur atoms into the existing sulphur-sulphur bond, for example by reaction with triphenylthiosulphenyl chloride in dichloromethane in the presence of acetic acid, as provided, for example, in *Tetrahedron Letters*, Volume 41, Issue 37, September 2000, pages 7169-7172.

When the A or $A_a$ radical represents a group

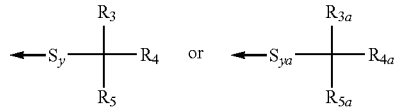

as defined above, the synthetic route can be similar to that described for the preceding compounds.

For example, Birch describes the oxidative coupling of methyl mercaptan with tert-butyl mercaptan in the presence of potassium hexacyanoferrate(III) (Birch et al. *Journal of the Institute of Petroleum*, 1953, vol. 39, pp. 206-210).

It is also possible to follow another procedure consisting in carrying out a redistribution reaction on a symmetrical disulphide in the presence of an alkyl mercaptan, as described, for example, by Brzezinska, Ewa and Ternay, Andrew L., Jr. in the paper *Disulfides Syntheses Using 2,2'-Dithiobis(benzothiazole)*, Journal of Organic Chemistry (1994), 59, 8239-8244. This method consists in reacting a symmetrical disulphide and a mercaptan, such as, for example, tert-butyl mercaptan, in chloroform, which results in a redistribution.

By this reaction, the derivatives in which y=1 are obtained. In order to obtain the compounds in which y is greater than 1, it is possible to insert sulphur atoms into the existing sulphur-sulphur bond, for example by reaction with triphenylthiosulphenyl chloride in dichloromethane in the presence of acetic acid, as provided, for example, in *Tetrahedron Letters*, Volume 41, Issue 37, September 2000, pages 7169-7172.

When the A radical represents a group

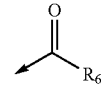

as defined above, this compound can be prepared according to a thioesterification reaction between the thiol and its corresponding thiolate with a carboxylic acid or its derivatives (acid chloride, anhydride) bearing the $R_6$ radical.

For example, Jan Larsen and Christine Lenoir in *Organic Syntheses, Coll.* Vol. 9, p. 72 (1998), describe a thioesterification reaction between a thiol and an acid chloride in the presence of triethylamine to trap the hydrochloric acid formed, the reaction being carried out in dichloromethane at between 0 and 10° C.

When the A or $A_a$ radical represents a group

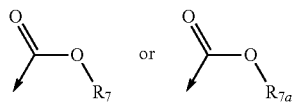

as defined above, this compound can be prepared by an addition/elimination reaction between the thiol and an alkyl chloroformate bearing the $R_7$ or $R_{7a}$ radical, which can itself either be commercially available or be prepared by reaction between an alcohol and phosgene or one of its derivatives. An organic or inorganic base can be added in order to trap the hydrochloric acid formed.

This approach is described by Taylor, Roger in *Journal of the Chemical Society, Perkin Transactions 2: Physical Organic Chemistry* (1972-1999), 1983, pp. 291-296. The authors react ethyl mercaptan with methyl chloroformate in the presence of pyridine.

Instead of using the thiol, it is possible to use the corresponding thiolate. This approach is described by Suzuki, Shigenori, Hisamichi, Kanehiko and Endo, Katsuya in *Heterocycles,* 1993, vol. 35, #2 pp. 895-900. The authors react sodium methylthiolate with methyl chloroformate in order to obtain the thiocarbonate derivative.

Another synthetic route consists in reacting the thiol or its thiolate with phosgene (Chen, H. W. et al., *Journal of the American Chemical Society,* 1978, vol. 100, pp. 2370-2375) or one of its derivatives, such as triphosgene (WO2008/038175), optionally in the presence of an inorganic or organic base, such as a tertiary amine, for example, in order to form the chlorothioformate intermediate. This intermediate can subsequently react with an alcohol in the presence of an organic base, such as a tertiary amine, in order to form the thiocarbonate compound. This approach is, for example, described in *Organic Syntheses, Coll.* Vol. 5, p. 166 (1973); Vol. 44, p. 20 (1964).

When the A or $A_a$ radical represents a group

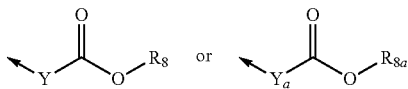

as defined above, this compound can be prepared by nucleophilic substitution between the thiol or its thiolate and an ester substituted by a halogen group and bearing the Y and $R_8$ or $Y_a$ and $R_{8a}$ radicals, such as, for example, bromoethyl acetate or methyl 4-bromobutyrate.

For example, the reaction between 3-mercapto-5,6-diphenyl-1,2,4-triazine and ethyl 3-bromopropionate in ethyl acetate in the presence of triethylamine, in order to trap the hydrobromic acid formed, is descibed by Bhalla, M., Srivastava, V. K., Bhalla, T. N. and Shanker, K. in *Bollettino Chimico Farmaceutico* (1995), 134(1), 9-15.

When the A or $A_a$ radical represents a group

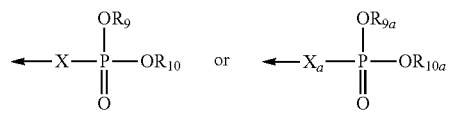

as defined above, this compound can be prepared by nucleophilic substitution between the thiol or its thiolate and a halogenated derivative of a phosphonate or of a phosphonic acid bearing the X, $R_9$ and $R_{10}$ or $X_a$, $R_{9a}$ and $R_{10a}$ radicals, and more particularly with a bromo-ou chloroalkylphosphonate.

This reaction is described, for example, for the reaction between diethyl (2-bromoethyl)phosphonate and sodium ethanethiolate in an ether (Mikolajczyk, Marian, Costisella, Burkhard and Grzejszczak, Slawomir, *Tetrahedron,* 1983, vol. 39, #7 pp. 1189-1193).

When the A or $A_a$ radical represents a group

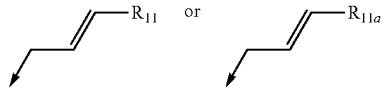

as defined above, this compound can be prepared by nucleophilic substitution between the thiol or its thiolate and an allyl halide bearing the $R_{11}$ or $R_{11a}$ radical, for example between the thiol and allyl bromide.

For example, the reaction between a triazinethiol and an allyl halide in the presence of potassium carbonate in alcohol is described in Patent BE 503980 of the Société Belge de l'azote et des produits chimiques du Marly (1951).

An example of a compound of formula (I) is 2-thiazolidinethione of formula,

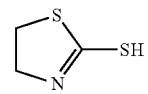

sold, for example, by Sigma Aldrich.

Another example of a compound of formula (I) is the compound of formula

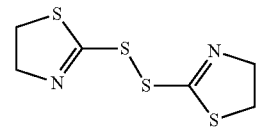 [SMILES: C1CSC(SSC2=NCCS2)=N1]

described in the document U.S. Pat. No. 3,379,678.

Mention may also be made of the compound of following formula

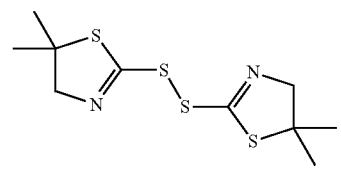

described in the document *Thiazolinephenols. 5-Methyl- and 5,5-dimethylthiazolinephenols, byproducts and derivatives*, Hart, Wm. F. and Niederl, Joseph B., *Journal of the American Chemical Society* (1939), 61, 1145-8.

III. Examples

A. Synthesis of Compound A:
2-(tert-butyldisulfanyl)-4,5-dihydrothiazole

The starting material is commercially available (Aldrich, CAS 96-53-7,2-thiazoline-2-thiol).

Compound A is prepared according to the following synthetic scheme:

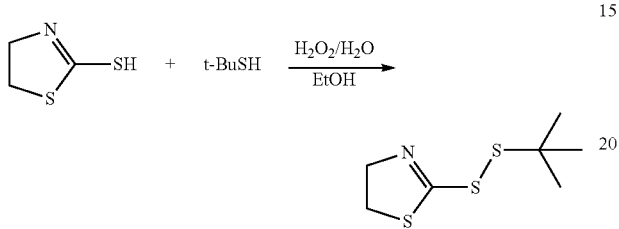

An $H_2O_2$ solution (5.0 ml, 0.040 mol, 30% in water) is added dropwise over a period of 80 minutes to a solution of 2-methyl-2-propanethiol (3.61 g, 0.040 mol) and 2-thiazoline-2-thiol (4.77 g, 0.040 mol) in ethanol (30 ml), so as to maintain the temperature of the reaction medium at 21° C. The reaction medium is stirred at this temperature for 2.0 hours. The mixture is subsequently diluted with petroleum ether (100 ml) and washed with a solution of $K_2CO_3$ (1.0 g) in water (50 ml). The organic phase is separated and then washed with water (4 times with 50 mol). The combined organic phases are evaporated under reduced pressure (Tbath 21° C., 7 mbar). A colourless liquid (5.83 g, 0.028 mol, yield 70.3%) is obtained.

The molar purity is greater than 95% ($^1$H NMR).

TLC: $R_f$=0.64 ($SiO_2$; heptane:EtOAc=1:1; visualization by UV and $I_2$).

NMR Characterization:

The chemical shifts obtained by $^1$H and $^{13}$C NMR in $d_6$-DMSO are given in the table below. The calibration is carried out with regard to DMSO (2.44 ppm in $^1$H and at 39.5 ppm in $^{13}$C).

| No., | δ $^1$H (ppm) | δ $^{13}$C (ppm) |
|---|---|---|
| 1 | 4.25 | 67.0 |
| 2 | 3.32 | 34.0 |
| 3 | / | 170.2 |
| 4 | / | 49.1 |
| 5 | 1.27 | 29.2 |

B. Composition Examples

1. Example 1

The object of this example is to compare the properties of a rubber composition comprising carbon black and silica, which can be used for the manufacture of a tyre tread, comprising MBTS as primary vulcanization accelerator (composition C1), with the properties of a rubber composition according to the invention comprising compound A (composition C2) as primary vulcanization accelerator.

The formulations of the compositions are given in Table 1 below. The amounts are expressed in parts per 100 parts by weight of elastomer (phr).

TABLE 1

| Tests | C1 | C2 |
|---|---|---|
| BR (1) | 30 | 30 |
| SBR (2) | 70 | 70 |
| Carbon black (N234) (3) | 4 | 4 |
| Silica (4) | 80 | 80 |
| 6-PPD (5) | 2 | 2 |
| Ozone wax C32 ST (6) | 1.5 | 1.5 |
| Resin (7) | 20 | 20 |
| Silane, liq. (8) | 6.5 | 6.5 |
| SAD (9) | 2 | 2 |
| DPG (10) | 1.5 | 1.5 |
| ZnO | 1.5 | 1.5 |
| Sulphur | 1.2 | 1.2 |
| MBTS* | 1.2 | — |
| Compound A | — | 1.5 |

(1) Polybutadiene with 0.7% of 1,2-; 1.7% of trans-1,4-; 98% of cis-1,4-(Tg = −105° C.) (mol %)
(2) Butadiene-styrene copolymer SSBR (SBR prepared in solution) with 25% of styrene, 59% of 1,2-polybutadiene units and 20% of trans-1,4-polybutadiene units (Tg = −24° C.) (mol %); content expressed as dry SBR (SBR extended with 9% by weight of MES oil, i.e. a total of SSBR + oil equal to 76 phr)
(3) Carbon black
(4) Silica "Zeosil 1165MP" from Rhodia, "HDS" type (BET and CTAB: approximately 160 m$^2$/g);
(5) Antioxidant 6-PPD
(6) Anti-ozonant
(7) Aliphatic resin (C$_5$ pure) "Hikorez A-1100", sold by Kolon
(8) Coupling agent
(9) Stearic acid: Stearin "Pristerene" from Uniqema
(10) Diphenylguanidine (Perkacit DPG from Flexsys)
*MBTS from G-QUIMICA, sold under the reference Rubator MBTS The rheometric properties at 150° C. are given in Table 2 below.

TABLE 2

| Tests | C1 | C2 |
|---|---|---|
| k | 0.59 | 0.42 |
| T0 (min) | 0.92 | 8.24 |

The rheometric properties obtained for the compositions according to the invention show that compound A can be used as vulcanization accelerator in rubber compositions comprising one or more reinforcing fillers.

2. Example 2

The object of this example is to compare the properties of a rubber composition comprising carbon black, which can be used for the manufacture of a tyre tread, comprising MBTS as primary vulcanization accelerator (composition C1), with the properties of a rubber composition according to the invention comprising different contents of compound (compositions C2 and C3) as primary vulcanization accelerator.

The formulations of the compositions are given in Table 3 below. The amounts are expressed in parts per 100 parts by weight of elastomer (phr).

TABLE 3

| Tests | C1 | C2 | C3 |
|---|---|---|---|
| NR (1) | 100 | 100 | 100 |
| Carbon black (N234) | 47 | 47 | 47 |
| SAD (2) | 2.5 | 2.5 | 2.5 |
| ZnO | 2.7 | 2.7 | 2.7 |
| Sulphur | 1.5 | 1.5 | 1.5 |
| MBTS (3) | 0.38 | — | — |
| Compound A | — | 0.47 | 0.24 |

(1) Natural rubber
(2) Stearin "Pristerene" from Uniqema
(3) MBTS from G-QUIMICA, sold under the reference Rubator MBTS The rheometric properties at 150° C. are given in Table 4 below.

TABLE 4

| Tests | C1 | C2 | C3 |
|---|---|---|---|
| k | 0.32 | 0.50 | 0.21 |
| T0 (min) | 1.21 | 4.83 | 4.11 |

The rheometric properties obtained for the compositions according to the invention show that compound A can be used as vulcanization accelerator in rubber compositions comprising one or more reinforcing fillers.

The invention claimed is:

1. A rubber composition for the manufacture of tires, based on one or more diene elastomers, on one or more reinforcing fillers and on a vulcanization system, wherein said vulcanization system comprises one or more thiazoline compounds chosen from the compounds of formula

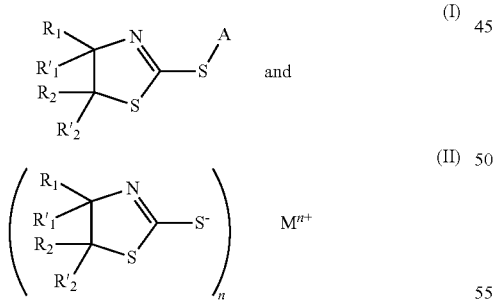

where:

$R_1$, $R_2$, $R'_1$ and $R'_2$ independently represent H or a $C_1$-$C_{25}$ hydrocarbon group chosen from linear, branched or cyclic alkyl groups, aralkyl groups, alkylaryl groups and aryl groups, $R_1$ can be combined with $R_2$ or $R'_2$ to form a non-aromatic ring, $R_2$ can be combined with $R_1$ or $R'_1$ to form a non-aromatic ring, A is chosen from H,

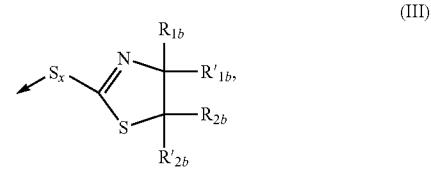

where in $R_{1b}$ is identical to $R_1$, $R_{2b}$ is identical to $R_2$, $R'_{1b}$ is identical to $R'_1$ and $R'_{2b}$ is identical to $R'_2$, and x is an integer greater than or equal to 1,

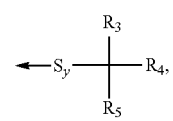

wherein $R_3$, $R_4$ and $R_5$ independently represent a $C_1$-$C_{18}$ hydrocarbon group which does not comprise a heteroatom, and y is an integer greater than or equal to 1,

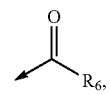

wherein $R_6$ is a $C_1$-$C_{18}$ hydrocarbon group, provided that $R_1$, $R_2$, $R'_1$ and $R'_2$ do not simultaneously represent H,

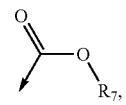

wherein $R_7$ is a $C_1$-$C_{18}$ hydrocarbon group,

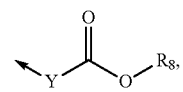

wherein Y is a $C_1$-$C_{18}$ hydrocarbon chain, and $R_8$ is a $C_1$-$C_{18}$ hydrocarbon group,

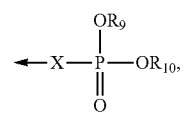

wherein X is a $C_1$-$C_{18}$ hydrocarbon chain, and $R_9$ and $R_{10}$ independently represent a $C_1$-$C_{18}$ hydrocarbon group, and

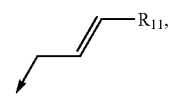

wherein $R_{11}$ is H or a $C_1$-$C_{18}$ hydrocarbon group, $M^{n+}$ represents a metal or non-metal cation, and n represents an integer varying between 1 and 4.

2. The composition according to claim 1, wherein $R_1$, $R_2$, $R'_1$ and $R'_2$ independently represent H or a methyl group.

3. The composition according to claim 2, wherein $R_1$, $R_2$, $R'_1$ and $R'_2$ each represent H.

4. The composition according to claim 2, wherein two radicals chosen from $R_1$, $R_2$, $R'_1$ and $R'_2$ represent a methyl group, the other two representing H.

5. The composition according to claim 1, wherein A is

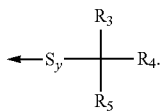

6. The composition according to claim 1, wherein the $R_3$ to $R_{11}$ groups are independently chosen from linear, branched or cyclic alkyl groups, aryl groups, aralkyl groups and alkylaryl groups.

7. The composition according to claim 1, wherein the X and Y groups are independently chosen from linear, branched or cyclic alkylene groups, arylene groups and alkylarylene groups.

8. The composition according to claim 1, wherein $M^{n+}$ is a metal cation chosen from $Zn^{2+}$, $Cu^{2+}$, $Na^+$, $K^+$ and $Li^+$.

9. The composition according to claim 1, wherein $M^{n+}$ is a non-metal cation.

10. The composition according to claim 1, wherein the said thiazoline compound or compounds represent from 0.1 to 7 phr (parts by weight per hundred of diene elastomer).

11. The composition according to claim 1, wherein the diene elastomer or elastomers are selected from the group consisting of polybutadienes, natural rubber, synthetic polyisoprenes, butadiene copolymers, isoprene copolymers and the mixtures of these elastomers.

12. The composition according to claim 1, wherein the reinforcing filler or fillers are chosen from silica, carbon black and their mixtures.

13. The composition according to claim 1, wherein the reinforcing filler or fillers are present at a content of between 20 and 200 phr.

14. A process for preparing a rubber composition for the manufacture of tires according to claim 1, said process comprising the steps of:
  incorporating the reinforcing filler or fillers in the said diene elastomer or elastomers during a first stage, the composition being kneaded thermomechanically, in one or more goes, until a maximum temperature of between 110° C. and 190° C. is reached; and
  subsequently incorporating, during a second stage, the crosslinking system and kneading the composition up to a maximum temperature of less than 110° C.

15. The process according to claim 14, wherein, between the steps, the composition is cooled to a temperature of less than or equal to 100° C.

16. A process of manufacturing a finished article or a semi-finished product comprising the step of:
  incorporating a composition according to claim 1 in the finished article or semi-finished product.

17. A finished article or semi-finished product comprising a composition according to claim 1.

18. A tire comprising a rubber composition according to claim 1.

19. A tread comprising a rubber composition according to claim 1.

20. A thiazoline of formula

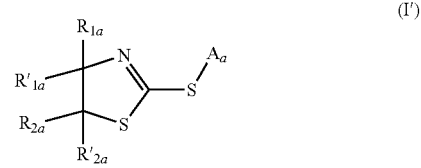

where:

$R_{1a}$, $R_{2a}$, $R'_{1a}$ and $R'_{2a}$ represent H or a $C_1$-$C_{25}$ hydrocarbon group chosen from linear, branched or cyclic alkyl groups, aralkyl groups, alkylaryl groups and aryl groups, $R_{1a}$ can be combined with $R_{2a}$, or $R'_{2a}$ to form a non-aromatic ring, $R_{2a}$ can be combined with $R_{1a}$ or $R'_{1a}$ to form a non-aromatic ring and $A_a$ is chosen from

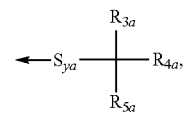

wherein $R_{3a}$, $R_{4a}$ and $R_{5a}$ independently represent a $C_1$-$C_{18}$ hydrocarbon group, and ya is an integer greater than or equal to 1,

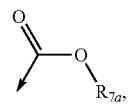

wherein $R_{7a}$ is a $C_1$-$C_{18}$ hydrocarbon group,

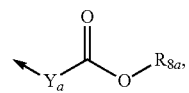

wherein $Y_a$ is a $C_1$-$C_{18}$ hydrocarbon chain, and $R_{8a}$ is a $C_1$-$C_{18}$ hydrocarbon group, provided that, if $R_{1a}$, $R_{2a}$, $R'_{1a}$ and $R'_{2a}$ simultaneously represent H, $Y_a$ is an $C_1$-$C_{10}$ alkylene chain and $R_{8a}$ is a $C_1$-$C_{10}$ alkyl group,

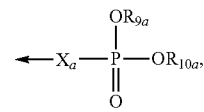

wherein $X_a$ is a $C_1$-$C_{18}$ hydrocarbon chain, and $R_{9a}$ and $R_{10a}$ independently represent a $C_1$-$C_{18}$ hydrocarbon group, and

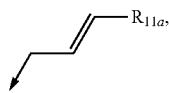

wherein $R_{11a}$ is H or a $C_1$-$C_{18}$ hydrocarbon group, provided that $R_{1a}$, $R_{2a}$, $R'_{1a}$ and $R'_{2a}$ represent a $C_1$-$C_{18}$ alkyl on a $C_3$-$C_{18}$ cycloalkyl group.

21. A process of manufacturing a rubber composition based on one or more diene elastomers, on one or more reinforcing fillers and on a vulcanization system, the process comprising the step of:

incorporating, as a vulcanization accelerator, a thiazoline according to claim 20.

22. The thiazoline according to claim 20, wherein $R_{1a}$, and $R_{2a}$, $R'_{1a}$ and $R'_{2a}$ independently represent H or a methyl group.

23. The thiazoline according to claim 22, wherein $R_{1a}$, and $R_{2a}$, $R'_{1a}$ and $R'_{2a}$ represent H.

24. The thiazoline according to claim 22, wherein two radicals chosen from $R_{1a}$, $R_{2a}$, $R'_{1a}$ and $R'_{2a}$ represent a methyl group and the other two radicals represent H.

25. The thiazoline according to claim 20, wherein $A_a$ is

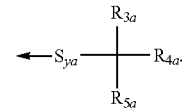

26. The thiazoline according to claim 20, wherein the $R_{3a}$ to $R_{5a}$ and $R_{7a}$ to $R_{11a}$ groups are independently chosen from linear, branched or cyclic alkyl groups, aryl groups, aralkyl groups and alkylaryl groups.

27. The thiazoline according to claim 20, wherein the $X_a$ and $Y_a$ groups are independently chosen from linear, branched or cyclic alkylene groups, arylene groups and alkylarylene groups.

* * * * *

UNITED STATES PATENT AND TRADEMARK OFFICE
CERTIFICATE OF CORRECTION

PATENT NO. : 9,550,891 B2
APPLICATION NO. : 14/111606
DATED : January 24, 2017
INVENTOR(S) : Anne Veyland et al.

It is certified that error appears in the above-identified patent and that said Letters Patent is hereby corrected as shown below:

On the Title Page

(56) FOREIGN PATENT DOCUMENTS
"BE 503980 A 6/1951" should be deleted.

(57) ABSTRACT
Line 1, "tyres" should read --tires--.

In the Specification

Column 18
Line 12, "$R_{1a}$," should read --$R_{3a}$,-- and "$C_1$-$C_{1s}$" should read --$C_1$-$C_{18}$--;
Line 39, "an" should read --a--; and
Line 62, "an" should read --a--.

In the Claims

Column 26
Line 11, "where in" should read --wherein--.

Column 28
Line 55, "an" should read --a--.

Column 30
Line 13, "$R_{5a}$" should read --$R_{5a}$--.

Signed and Sealed this
Seventh Day of November, 2017

Joseph Matal
*Performing the Functions and Duties of the
Under Secretary of Commerce for Intellectual Property and
Director of the United States Patent and Trademark Office*